(12) United States Patent
Abunassar et al.

(10) Patent No.: US 9,861,504 B2
(45) Date of Patent: Jan. 9, 2018

(54) SYSTEM AND METHOD FOR RENAL NEUROMODULATION BY ADJUSTABLE OVERSIZED STENT

(71) Applicant: Abbott Cardiovascular Systems Inc., Santa Clara, CA (US)

(72) Inventors: Chad Abunassar, San Francisco, CA (US); Denis Tauz, Los Gatos, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 42 days.

(21) Appl. No.: 15/081,757

(22) Filed: Mar. 25, 2016

(65) Prior Publication Data

US 2017/0273807 A1    Sep. 28, 2017

(51) Int. Cl.
*A61F 2/06* (2013.01)
*A61F 2/844* (2013.01)
*A61F 2/915* (2013.01)

(52) U.S. Cl.
CPC .............. *A61F 2/844* (2013.01); *A61F 2/915* (2013.01); *A61F 2002/91558* (2013.01); *A61F 2210/009* (2013.01); *A61F 2250/0001* (2013.01); *A61F 2310/00011* (2013.01)

(58) Field of Classification Search
CPC ...... A61F 2/86; A61F 2/82; A61F 2/06; A61F 2/915; A61F 2250/001; A61F 2250/0071; A61B 2018/00511
See application file for complete search history.

(56) References Cited

U.S. PATENT DOCUMENTS

| | | |
|---|---|---|
| 779,035 A | 1/1905 | Fladby et al. |
| 5,722,401 A | 3/1998 | Pietroski et al. |
| 6,155,264 A | 12/2000 | Reesemann et al. |
| 6,238,421 B1 | 5/2001 | Gunther et al. |
| 6,293,955 B1 | 9/2001 | Houser et al. |
| 6,475,233 B2 | 11/2002 | Trozera |
| 6,542,781 B1 | 4/2003 | Koblish et al. |
| 6,623,452 B2 | 9/2003 | Chien et al. |
| 6,802,857 B1 | 10/2004 | Walsh et al. |
| 7,708,715 B2 | 5/2010 | Gellman |
| 7,918,883 B2 | 4/2011 | Weber |
| 7,972,371 B2 | 7/2011 | Martin |
| 8,043,257 B2 | 10/2011 | Nguyen et al. |
| 8,131,371 B2 | 3/2012 | Demarals et al. |
| 8,412,346 B2 | 4/2013 | Gellman et al. |
| 8,473,067 B2 | 6/2013 | Hastings et al. |
| 2004/0138738 A1 | 7/2004 | Stinson |
| 2005/0059931 A1 | 3/2005 | Garrison et al. |

(Continued)

*Primary Examiner* — Brian Dukert
(74) *Attorney, Agent, or Firm* — David J. Pitman; Fulwider Patton LLP

(57) ABSTRACT

A method for treating a patient diagnosed with a cardio-renal disease or disorder, the method comprising selecting a span of a renal artery having a first internal diameter, an artery wall; selecting a self-expanding stent having a cylindrical outer surface, the stent being configured to have a first external diameter in an unexpanded condition and being capable of expanding to have a second external diameter; implanting the stent in the span of the renal artery, and applying pressure to the at least one renal nerve with the stent, thereby at least partially modulating a function of the at least one renal nerve; then, reducing an elastic modulus of the stent when the stent has the second external diameter.

7 Claims, 8 Drawing Sheets

(56) References Cited

U.S. PATENT DOCUMENTS

| | | |
|---|---|---|
| 2009/0093791 A1 | 4/2009 | Heuser |
| 2009/0182404 A1 | 7/2009 | Shokoohi |
| 2011/0182912 A1 | 7/2011 | Evans et al. |
| 2012/0150282 A1 | 6/2012 | Adden et al. |
| 2013/0245621 A1 | 9/2013 | Persson et al. |
| 2014/0343590 A1* | 11/2014 | Solem ................ A61B 17/32 606/185 |

\* cited by examiner

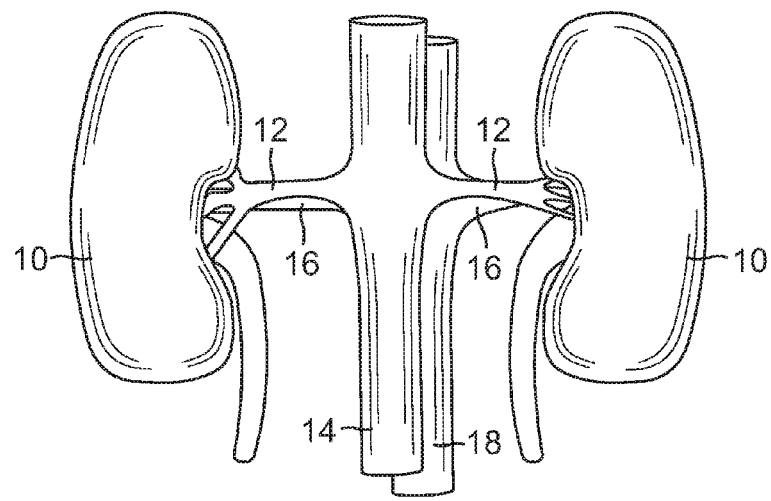
FIG. 1
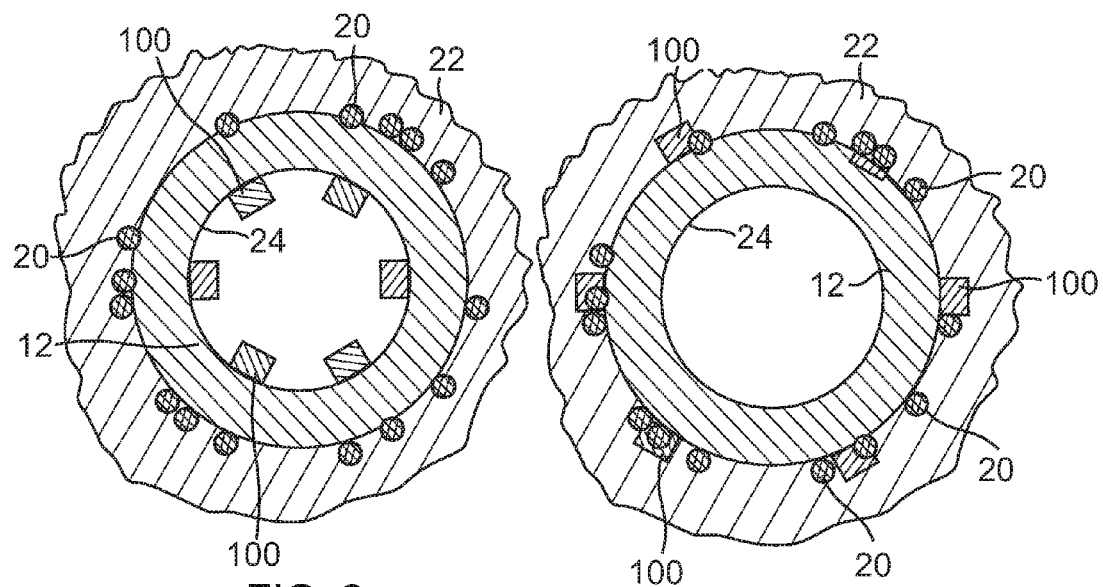
FIG. 2
FIG. 3

SYSTEM AND METHOD FOR RENAL NEUROMODULATION BY ADJUSTABLE OVERSIZED STENT

RELATED APPLICATIONS

This application is a continuation-in-part of, application Ser. No. 14/918,191 the contents of which are incorporated herein in their entirety.

BACKGROUND

This invention relates to methods and devices for treatment of diseases that include congestive heart failure, chronic renal failure and hypertension. Specifically, the invention relates to improving conditions in patients by blocking or at least modifying (modulating) signals via the renal nerve.

Heart Failure

Congestive Heart Failure (CHF) is a form of heart disease that is becoming ever more common. The number of patients with CHF is expected to grow in increasing numbers as the so-called "Baby Boomers" reach 50 years of age. CHF is a health condition that occurs when the heart becomes damaged, resulting in a reduced blood flow to the organs of the body. If blood flow decreases sufficiently, kidney function becomes impaired and results in fluid retention, abnormal hormone secretions and increased constriction of blood vessels. These results increase the stress on the heart to do work, and further decrease the capacity of the heart to pump blood through the kidney and vascular circulation system. This reduced capacity further reduces blood flow to the kidney. It is believed that this cycle of reduced kidney perfusion is the principal non-cardiac cause perpetuating a patient's downward spiral into CHF. Moreover, the fluid overload and associated clinical symptoms resulting from these changes are predominant causes for excessive hospital admissions, reduced quality of life and overwhelming costs to the health care system.

While many different diseases may cause initial damage to the heart, once such damage is present, CHF is identifiable under two types: Chronic CHF and Acute CHF. Despite its name, the chronic form is the less acute form of the two but is a longer term, slowly progressive, degenerative disease, and may lead to cardiac insufficiency. Chronic CHF is clinically categorized by the patient's mere inability to exercise or perform normal activities of daily living.

By contrast, patients with Acute CHF may experience a more severe deterioration in heart function than those with Chronic CHF. The Acute form results in the inability of the heart to maintain sufficient blood flow and pressure to keep vital organs of the body alive. This condition can occur when extra stress (such as by infection) significantly increases the workload on the heart in a patient with an otherwise stable form of CHF. By contrast to a mere stepwise downward progression that is observable in patients with Chronic CHF, a patient suffering Acute CHF may deteriorate rapidly from even the earliest stages of CHF to severe hemodynamic collapse. Moreover, Acute CHF can occur within hours or days following an Acute Myocardial Infarction (AMI), which is a sudden, irreversible injury to the heart muscle, identified in common parlance as a heart attack.

Kidney Failure

Against this background, the kidneys are known to play an important regulatory role in maintaining the homeostatic balance of the body. The kidneys eliminate foreign chemicals from the body, regulate inorganic substances, and function as endocrine glands to secrete hormonal substances like renin and erythropoietin. The main functions of the kidney are to maintain the water balance of the body and control metabolic homeostasis by making the urine more or less concentrated, thus either reabsorbing or excreting more fluid. However, when renal disease arises, some otherwise ordinary and regular physiological functions may become detrimental to the patient's health. When this occurs, the process is known as overcompensation. In the case of Chronic Renal Failure (CRF) the event of overcompensation may manifest itself as hypertension that has the effect of damaging the heart and blood vessels, and can eventually result in a stroke or death. Thus, without proper function by the kidneys, a patient may suffer water retention, reduced urine flow and an accumulation of waste toxins in the blood and body. These conditions resulting from reduced renal function, or renal failure (kidney failure), tend to increase the workload placed upon the heart. In a patient, simultaneous occurrence of both CRF and CHF may cause the heart to further deteriorate as the water build-up and blood toxins accumulate due to the poorly functioning kidneys and may, in turn, cause the heart further harm.

Nervous System

It has been observed, in connection with human kidney transplantation, that there is evidence to suggest that the nervous system plays a major role in kidney function. It was noted for example that after a transplant, when all the renal nerves are severed, the kidney was observed to increase excretion of water and sodium. This phenomenon has also been observed in animals when renal nerves are cut or chemically destroyed. The phenomenon has been termed "denervation diuresis" because the denervation acted on a kidney in a similar way to a diuretic medication. Later, observation of "denervation diuresis" was found to be associated with the vasodilatation of the renal arterial system that led to the increase of the blood flow through the kidney. This observation was confirmed by the observation in animals that reducing blood pressure supplying the kidney could reverse the "denervation diuresis".

It was also observed that after several months passed after the transplant surgery in successful cases, the "denervation diuresis" in transplant recipients stopped, and the kidney function returned to normal. Initially, it was believed that "renal diuresis" is merely a passing phenomenon and that the nerves conducting signals from the central nervous system to the kidney are not essential for kidney function. Later discoveries led to the present generally held conclusion that the renal nerves have an ability to regenerate, and that the reversal of the "denervation diuresis" is attributable to the growth of the new nerve fibers supplying kidneys with the necessary stimuli.

In summary then, it is known from clinical experience and also from the large body of animal research that stimulation of the renal nerve leads to the vasoconstriction of blood vessels supplying the kidney, decreased renal blood flow, decreased removal of water and sodium from the body and increased renin secretion. It is also known that reduction of the sympathetic renal nerve activity, achieved by denervation, can reverse these processes.

Steps Taken in the Prior Art, and Problems Arising

There has therefore already been identified a need in the art for methods and devices that may apply the observed effects set forth above to halt and reverse the symptoms of Congestive Heart Failure. Thus, certain methods and devices have already been commercialized in the art to reduce renal nerve activity, in order to meet the aforesaid need. For example, the following patents are directed to the stated need: U.S. Pat. Nos. 7,620,451, 6,978,174, and 8,145,316, all of which are incorporated herein by reference. In some approaches configured to induce selective damage to the renal nerves (renal denervation), manufacturers have developed and used radio frequency (RF) catheters, or drug delivery devices, which, while being minimally invasive, have tradeoffs in terms of ease of use, treatment accuracy, and regulatory complexity. An additional problem is that some patients may require a follow-up treatment with these treatments in cases where nerves are not adequately disrupted after receiving initial denervation therapy, and this introduces the complexity of having to apply multiple treatments over a period of time for the same condition.

Thus there is today an additional need to overcome the limitations and challenges of contemporary RF-based renal denervation therapy. RF contact requires energy transmission through contact with the targeted tissue. The manner of contact affects the intensity of RF energy transmission, wherein a smaller contact surface is desired to produce intensified tissue and nerve ablation. Once RF ablation has begun, tissue in the vicinity of a contact surface becomes desiccated as water molecules are induced into a vibrational state to the point of generating substantial heat within the tissue. An injury response is subsequently induced, and this has been shown to disrupt neural pathways passing through the zone of injury. However, some problems with contemporary RF methods for renal denervation are included in the list set forth here: (1) Renal artery bending motion may make accurate catheter-to-vessel contact difficult to reliably control, and therefore may make it difficult to control the degree and location of the desired RF-based injury; (2) Many point-based RF catheters only denervate a single contact point at a time, and cannot reliably guarantee the disruption of nerves around the entire renal artery circumference; (3) To accommodate problem no. 2, single point-based RF therapy has been developed, but this generally requires multiple ablations with targeted positions around the circumference of the renal artery; this is thought to increase the likelihood of disrupting the bundle of nerves passing by the renal artery; (4) If RF induced injury is too intensely localized within a short span of artery, there is a possibility of arterial occlusion or thrombosis.

In order to manage the above challenges, drug-driven therapies have been introduced to locally deliver chemical agents to induce injury to the renal nerves in the peri-adventitial space. However, these "combination device" therapies are costly and require extensive regulatory cost to facilitate approval.

Need in the Art

Thus, there is a need in the medical arts to produce a therapy which is relatively simple, accurate, effective, and/or requires less costly existing equipment and methods. The present invention addresses these and other needs.

SUMMARY OF THE INVENTION

In an embodiment the invention is a method for treating a patient diagnosed with a cardio-renal disease or disorder. The method comprises initially selecting a span of a renal artery in the patient for implantation of a self-expanding stent, the renal artery having a first internal diameter, an artery wall, and being surrounded by a peri-adventitial space through which at least one renal nerve extends. The first internal diameter is measured. Then, a self-expanding stent having a cylindrical outer surface is selected, the stent being configured to have a first external diameter in an unexpanded condition and being capable of expanding to have a second external diameter, wherein the second external diameter once the stent is implanted within the artery, is larger than the first internal diameter. Then, the stent is implanted in the span of the renal artery, whereby the stent eventually expands towards the second external diameter and thereby passes through the artery wall to become embedded in the peri-adventital space surrounding the artery. The stent is allowed to apply pressure to the at least one renal nerve, and further allowed to thereby at least partially modulate a function of the at least one renal nerve. Upon allowing the function of the at least one nerve to be modulated, the elastic modulus of the stent when the stent has the second external diameter is reduced. This tends to have the effect of reducing the outward expansion force of the stent, and to reduce pressure on the at least one renal nerve.

In some embodiments, reducing an elastic modulus of the stent includes heating a portion of the stent. In turn, heating a portion of the stent may include applying an electromagnetic field, or an ultrasonic energy, or a radio frequency signal to the stent. Further, in embodiments, heating a portion of the stent includes positioning a metal element in a structural component of the stent.

In yet further embodiments, reducing an elastic modulus of the stent includes reducing an elastic modulus of the stent to a level at which the stent fractures.

By these embodiments, a surgeon user is given additional control over the expansion of the stent, and has the ability to terminate or reduce the outward expansive force.

In yet another embodiment, the invention is a stent. The stent comprises a plurality of rings formed from a material having a first magnetic resonance susceptibility, wherein, each ring comprises struts that extend generally parallel with an axis of the stent, each strut being connected to an adjacent strut at an upper end of the strut by a curved peak, and at a lower end of the strut by a curved valley. further wherein, each ring is connected to an adjacent ring by at least one link. Into this structure, there is inserted at least one plug, which is inserted into a hole formed in the stent, the plug being formed of a material having a second magnetic resonance susceptibility that is greater than the first magnetic resonance susceptibility.

In some embodiments, the stent is a self-expanding stent. It may be formed from a metal, and in other embodiments it may be formed from a polymer. In some embodiments, the at least one plug is positioned in a peak. In other embodiments, the at least one plug is positioned in a valley. When located in the peak or the valley, the plug is located in the portion of the stent to which the greatest bending stresses will be applied, and therefore, will affect the outward forces imparted by the stent to a great extent when the at least one plug is heated.

BRIEF DESCRIPTION OF THE DRAWINGS

FIG. 1 is a schematic drawing of human anatomy showing a site that is suitable for implantation of an aggressively oversized stent having features of the present invention.

FIG. 2 is a schematic sectional view of an body lumen into which a stent having features of the present invention is implanted, and before the stent expands to pass through the wall of the lumen.

FIG. 3 is a schematic sectional view of the body lumen and stent in FIG. 2, showing the stent after it has migrated through the wall of the lumen.

DETAILED DESCRIPTION OF SOME EMBODIMENTS

Figure 4A:
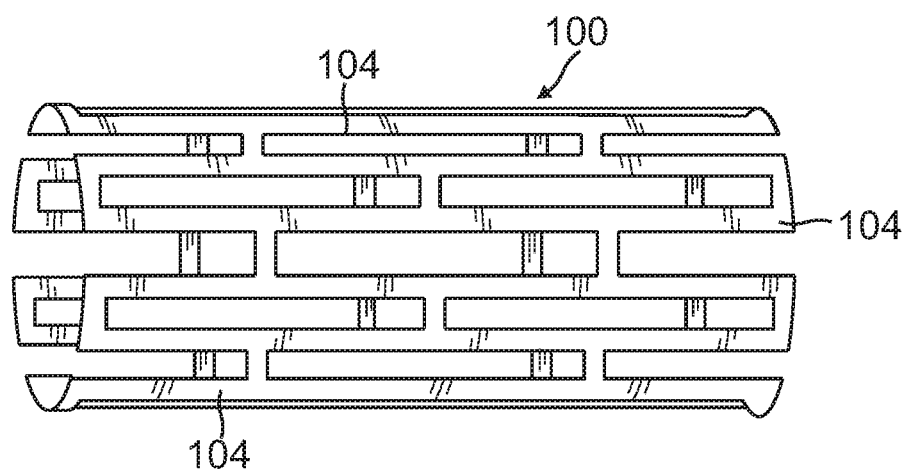
FIG. 4A is a perspective view of a stent having features according to the present invention.

In conjunction with the figures, preferred embodiments having features of the invention are described. In one embodiment, the invention is a system and method for producing controlled damage to nerves surrounding a vessel which may be a vein or artery. As explained above, such damage, where appropriately carried out to the renal nerves, is configured to have an impact that imparts therapeutic effects to the body of a patient that outweigh the effects of the damage to the nerve itself.

With reference to FIG. 1, the human renal anatomy includes kidneys 10 that are supplied with oxygenated blood by renal arteries 12, which are connected to the heart by the abdominal aorta 14. Deoxygenated blood flows from the kidneys to the heart via renal veins 16 and the inferior vena cava 18.

FIG. 2 illustrates a sectional view through a renal artery. More specifically, the renal anatomy also includes renal nerves 20 extending longitudinally along the lengthwise dimension of renal artery 12 generally within the adventitia, or peri-adventitial space 22 (also referred to herein as peri-adventital tissue or adventitia), surrounding the artery 12.

In accordance with the principles of the invention, a novel device-driven therapy is presented to produce minimally invasive denervation for the purpose of hypertension management. The method of this embodiment presents a novel approach for disrupting sympathetic nerve function (denervation) by the implantation of an oversized and high-radial strength scaffold in the renal artery. With reference to the figures, it is disclosed how, to simplify treatment and manage the above mentioned tradeoffs, a novel inventive system and method is presented wherein a sufficiently high radial strength stent 100 is implanted in the renal artery 12 in a span of the artery surrounded by critical sympathetic nerves 20. This scaffolding stent is designed so that, when implanted, the stent has a substantial excess of chronic outward force. As a result, it is configured to encourage stent strut migration, over a period of time after implantation, through the arterial wall 24 and into the peri-adventitial space 22. This effect is demonstrated with reference to FIG. 2 and FIG. 3. FIG. 2 shows a sectional view of a self-expanding stent according to an embodiment of the invention, having just been implanted in the renal artery. FIG. 3 shows the same stent some weeks or months later, having migrated through the wall 24 of the renal artery, to a location within the peri-adventitial space. The known physical phenomenon by which the stent may migrate through the wall 24 into the pre-adventitial space 22 is described below. As exemplified in FIG. 3, some stent struts are in close contact with, and press up against, some renal nerves 20, thereby applying mechanical pressure on the nerve.

The simple presence of the struts of a stent so implanted and configured for migration into this nerve-rich region, when combined with kidney motion during breathing, is configured to bring denervating effect and disruption to the signals and function of those nerves 20 which are brought into contact with the stent. In a further embodiment of the invention, if further denervation is required after treatment, another scaffold may be implanted to induce further disruption to the nerves occupying the peri-adventitial space surrounding the renal artery.

Experimental Support for Feasibility of the Invention

The phenomenon by which stent struts of a substantially oversized stent pass through the vascular wall into peri-adventitial space surrounding the vessel has been well observed, and recorded in medical literature. It has been noted to occur within a period of a few months, typically from four to eight months. Following hereunder are summaries of two exemplary published references (incorporated herein by reference) which demonstrate that it is possible to safely design a stent (for example, a coil, weaved 'wall-stent' style, or Nitinol tube-based stent) which is configured to penetrate through arterial intima and media and into the adventitia with good clinical outcomes:

Hong et al, Coronary Artery Disease. 1997 January: 8(1):45-8—Acute And Chronic Effects Of Self-Expanding Nitinol Stents In Porcine Coronary Arteries. In this report, results are identified in which all of a number of self-expanding stents were successfully deployed, and remained patent acutely. Three undersized stents migrated proximally and there was one episode of subacute thrombosis in an oversized stent. The remaining stents were patent throughout the survival period and neointimal responses were favorable for up to six months. There was evidence of continuing stent expansion over time and the majority of stent struts had migrated into the adventitial space by six months. Re-endothelization occurred starting one week after implantation and was complete by eight weeks.

Von Birgelen et al, American Journal of Cardiology. 1998 Jul. 15; 82(2):129-34.—Coronary Wallstents show significant late, postprocedural expansion despite implantation with adjunct high-pressure balloon inflations. In this report it is recorded that adjunct high-pressure balloon inflations following the delivery of oversized self-expandable so-called Wallstents may affect their implied late, postprocedural self-expansion. Fifteen so-called Wallstents were examined, which were implanted following a strategy of stent oversizing and subsequent adjunct high-pressure balloon inflations. The excellent radiographic visibility of this stent permitted reliable quantitative coronary angiographic measurement of both lumen and stent dimensions before and after stenting, and at follow-up. At follow-up, the extent and distribution of in-stent neointimal proliferation were evaluated with volumetric intravascular ultrasound. Between post-intervention and follow-up examination, the mean stent diameter increased from 3.7+/−0.4 to 4.2+/−0.4 mm. It was found that, despite high-pressure implantation, the subject Wallstents showed significant late self-expansion, which resulted in larger stent dimensions at follow-up that assisted in accommodating in-stent neointimal proliferation. Conversely, late stent expansion had a significant relation to the extent of in-stent neointimal ingrowth.

Structure of Some Embodiments

In some embodiments for achieving the system and method of the invention, a self-expanding stent that may have a structure similar to that exemplified in FIG. 4A having features of the present invention is configured to include the use of a stent having sufficient self-expanding radial outward force to gradually pass through arterial tissue after deployment. Preferably, the stent's diameter is selected to be over-sized in relation to the vessel diameter into which it is to be implanted, and to have sufficient oversize ratio to enable a stent diameter that is about 2 mm, and in some embodiments between 2 mm and 4 mm larger than the arterial wall diameter after the stent has been implanted in the artery. In some embodiments, the stent will be formed from super elastic and/or shape-memory material. For example, in some embodiments, a Nitinol (Nickel-Titanium) stent may be used to accomplish the desired attributes. Increased radial strength may be accomplished through the use of substantial strut radial depth.

It will be appreciated that, in order to achieve a stent diameter that is larger than 2 mm (between 2 mm and 4 mm) outside the arterial wall after the stent has been implanted in the artery and migrated beyond the arterial wall, it will be necessary to select a stent that has a naturally expanded diameter (i.e. expanded without any constraint at all) which is even larger than the desired final implanted diameter. As will be appreciated by those of ordinary skill, this is because, even if the stent is selected to be aggressively oversized in relation to the artery it is to be implanted in, its final implanted diameter within the peri-adventitial space will be smaller than its naturally expanded diameter—due to the restraining forces applied by the vessel wall which will prevent the stent from reaching its full unrestrained diameter.

Figure 6:
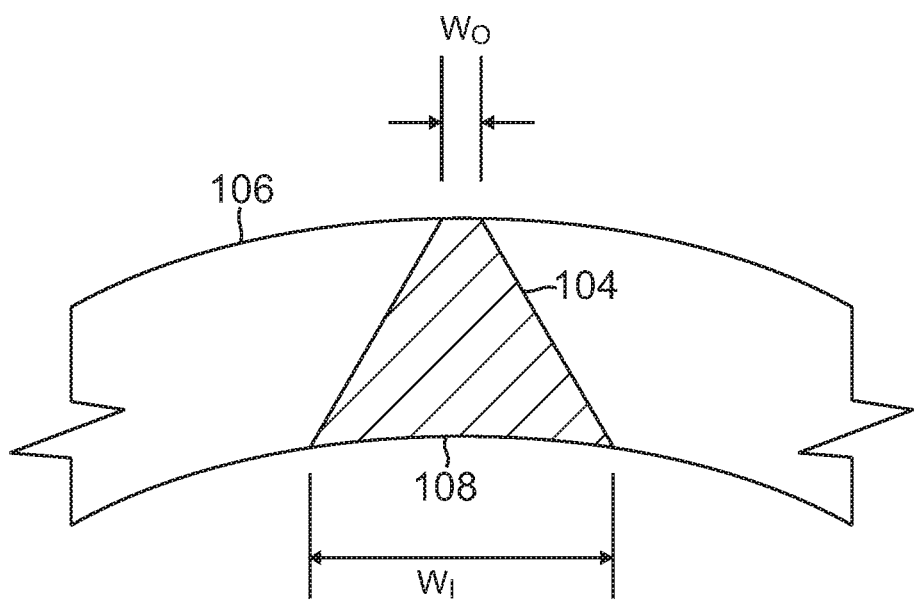
FIG. 6 is a detail view, in partial section, of portion of an embodiment of the stent in FIG. 4A or FIG. 4B.

In some embodiments, struts 104 of the stent 100 may be shaped to facilitate migration, or enhance the degree of migration, through the wall of the vessel, and thence through the tissue surrounding the vessel into the peri-arterial space. In order to accomplish this result, struts 104 of the stent may be cut during manufacture to have a shape that presents a narrower edge width $W_O$ on the outside surface 106 of the stent than the edge width $W_I$ on the inside surface 108 of the stent, as is exemplified in FIG. 6. Cutting a stent to have this described shape may be accomplished by orienting a laser beam, configured to cut the stent during manufacture, along a non-radial path from the outside of the stent. It will be appreciated that maintaining a non-radial orientation of the laser beam will require a complex operation of repositioning the source of the laser beam, or having more than one laser beam source, but that such complexity may be reduced if the stent itself is configured to have a simple shape with a minimum of twists and turns, such as exemplified by the stent in FIG. 4A.

In some embodiments, the shape of the stent struts described above may be temporarily masked by a suitable soluble coating, designed to slowly dissolve in the arterial environment. Such a coating may be formed from known drug eluting compounds such as a rapamycin derivative drug. Such drugs are described in the application U.S. Ser. No. 13/789,473 which is currently co-owned herewith. Thus, in use, the stent may be initially delivered to a desired location with such a coating adhering to the stent struts. The coating has the result that a broader surface of the coated stent is presented to the arterial wall than would be presented by the surface of the naked strut alone. Then, as the coating slowly dissolves in the arterial environment, the shape of the naked struts as described above is exposed to the arterial wall, and the degree of migration process is speeded up due to the angled shape of the struts. In this way, the rate of migration into the arterial wall may be slowed initially by the presence of the coating, in order to allow the stent to settle into position. Once the coating has dissolved sufficiently, the rate of migration may accelerate to accomplish the objective of the invention.

Advantages

As will be apparent to those of ordinary skill, the system and method of the invention will provide the following advantages over presently used methods of neuromodulation. First, an oversized stent for aggressive expansion into the neo-intimal zone and beyond into the adventitial space of the renal artery will provide continuous circumferential nerve disruption or modulation around the renal artery. This feature overcomes the spatial problem inherent in the need to frequently reposition a point electrode or drug injection. The invention provides ease of delivery, with little or no additional substantial physician training required, especially for those already competent with renal artery stenting.

Fragmentation

Figure 4B:
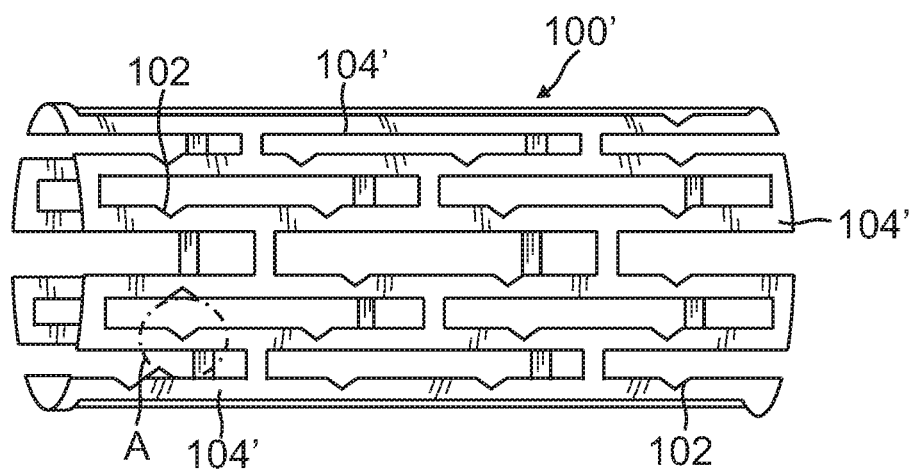
FIG. 4B is a perspective view of a stent having features according to another embodiment the invention.

In some embodiments of the invention, as exemplified in FIG. 4B, the implanted stent 100 may be designed with narrowed sections or notches 102 which are prone to fatigue failure in bending modes. These device fractures, which are configured to occur under excessive repeated bending modes associated with kidney motion due to inspiration and expiration, are configured to bring about exacerbated nerve disruption due to increased inflammation associated with independently movable strut motion. In this embodiment, the presence of fractured stent struts in the peri-adventitial space is configured to disrupt or modulate neural function by inducing sharpened pressure on the nerves and surrounding tissues, such sharpened pressure being applied by independently movable strut portions that have fractured and broken away from the original stent. Additionally, due to renal artery bending deformations associated with patient breathing cycles, the stent's broken struts are configured to repeatedly interact with nerves in the peri-adventitial space, thereby inducing cumulative injury or modulation and inflammation locally to the nerves surrounding the renal artery.

Figure 5:
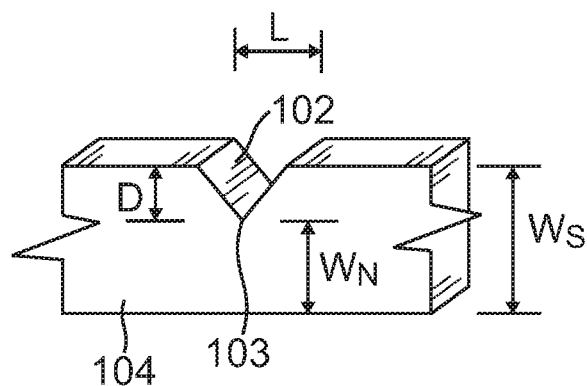
FIG. 5 is a detail view of a feature of the stent shown in FIG. 4B, taken from the area marked as "A."

Preferably, as exemplified in detail in FIG. 5, a narrowed section defines a notch 102 in the circumferential width of a strut 104 of the stent, the notch introducing a sharp corner 103 that is configured to provide a location of eventual stress fracture during bending through the known process of crack propagation. In some embodiments, the depth "D" of the notch, when material is removed from the width Ws of the strut, leaves a strut width Wn at the location of the notch which is in some embodiments about 50% of the strut width Ws. Each notch may have a length "L", as measured along the axial length of the stent. Moreover, a plurality of such notches 102 may be introduced into the struts along the length of the stent. Under this configuration, the strut at the location of the notch shall experience slight bending oscillations when positioned in the artery, and while the stent migrates through the wall of the artery, caused by the movement of the patient through inhalation and exhalation and other physical movement, such as may be caused by cardio vascular movement. The precise shape of a notch is preferably configured to increase the tendency of the strut at the location of at least some of the notches to fracture by fatigue failure in a timeframe after the stent has migrated through the wall of the artery. One of ordinary skill in the art would understand that the precise notch configuration required to produce this effect may be determined by experimentation, preferably by using a methodology including the following steps.

The following sets forth an exemplary experimental process by which an appropriate notch for the purpose may be configured. First, an assessment may be made of the amount of time required for the stent to pass through the wall of the artery and into the peri-adventitial space. It is believed that about six months is required for this process to take place. Next, the number, N, of bending oscillations that are likely to occur in this period may be determined. Assuming that inhalation and exhalation are the major causes of bending, it may be fair to assume that an inhalation to exhalation rate of ten cycles per minute is normal for an adult person. Thus, the designer of the stent would conclude that about 2.6 million cycles will take place in six months, and this number should be permitted to take place before fracture at the location of the notches becomes a probability. In other words, after 2.6 million cycles, the stent should have migrated through the artery wall and into the peri-adventitial space, and, after this timeframe, fracture would be desirable.

Then, it will be necessary for the designer to determine the magnitude of bending displacement that can be expected to occur in an average breathing cycle. An estimated movement of the stent within the artery may reasonably be assessed by affixing a known strain gauge system on a stent that is then implanted in an artery within an experimental canine subject, and measuring the strains and displacements that occur during a breathing cycle of the subject animal. For purposes of designing a stent under an embodiment of the present invention, such movement may reasonably be extrapolated to occur within a human subject.

Next, it will be necessary for the stent designer to conduct measurements to determine the shape of the notch in a strut that will be subjected to the anticipated fatigue loading. Having determined the displacement function that the stent may be expected to experience during the timeframe of being implanted in the subject human renal artery, a designer may apply to a notch of iteratively selected shape a fatigue test of known "S-N" variety, in which expected displacement is applied to a strut defining a notch, and measuring the number, "N," of cycles it takes to fracture the strut at the location of the notch. The designer may be obliged to iteratively alter the shape of the notch, giving it a more or less sharp angle, and/or a larger or smaller internal radius of curvature, and/or a greater or smaller width, until such time as the measured number "N" reaches the number estimated for fracture at the desired time—which is preferably six months under one embodiment of the invention. When the empirically determined number "N" which is associated with a particular notch configuration matches the estimated 2.6 million cycles in the course of iteratively altering the shape of the notch, a suitable shape for the notch may have been suitably identified. Having thus identified the shape of the notch, the designer may introduce this shape into a stent configured for implantation in a patient in order achieve the desired result.

Absorption

In yet a further embodiment of the invention, the scaffold struts of the oversize stent may be configured to be absorbed into the body of a patient in a time framework after substantial denervation has occurred. The configuration of material for bioabsorption after implantation in a patient is a field that has been developed to a relatively high degree of sophistication, as disclosed for example in U.S. Pat. Nos. 8,172,897, 7,875,283, and 7,956,100 which are incorporated herein by reference. As indicated by these and other prior art references, it is known in the art how to fabricate an implantable scaffold that will, after a period of time, experience bio-erosion and effectively dissolve entirely or substantially away from the location in which it has been implanted. Under the present embodiment of the invention in which an aggressively oversized scaffold is manufactured from bioerodable material, an advantage is provided in that, should the patient require further treatment by oversize scaffold after a first oversize stent scaffold has been implanted for renal denervation, a second implanted oversize scaffold migrating through the vessel wall will tend not to encounter a first implanted scaffold already in place, where it may otherwise interfere with and prevent the second scaffold from reaching the nerves surrounding the artery.

In application of the present embodiment, some metals are considered bioerodable since they tend to erode or corrode relatively rapidly when exposed to bodily fluids. Biostable metals refer to metals that are not bioerodable. Biostable metals have negligible erosion or corrosion rates when exposed to bodily fluids. In general, metal erosion or corrosion involves a chemical reaction between a metal surface and its environment. Erosion or corrosion in a wet environment, such as a vascular or peri-vascular environment, results in removal of metal atoms from the metal surface. The metal atoms at the surface lose electrons and become actively charged ions that leave the metal to form salts in solution. A bioerodable material suitable for use as a stent material are selected to form erosion products that do not negatively impact bodily functions.

Representative examples of biodegradable metals that may be used to fabricate an implantable medical device may include, but are not limited to, magnesium, zinc, and iron. In one embodiment of the invention, a bioerodable metal stent may be completely eroded when exposed to bodily fluids, such as blood, over a period of between about a week and about three months, or more narrowly, between about one month and about two months.

Representative examples of polymers that may be used to fabricate an implantable stent using the methods disclosed herein include, but are not limited to, poly(N-acetylglucosamine) (Chitin), Chitoson, poly(hydroxyvalerate), poly (lactide-co-glycolide), poly(hydroxybutyrate), poly(hydroxybutyrate-co-valerate), polyorthoester, polyanhydride, poly(glycolic acid), poly(glycolide), poly(L-lactic acid), poly(L-lactide), poly(D,L-lactic acid), poly(D,L-lactide), poly(caprolactone), poly(trimethylene carbonate), polyester amide, poly(glycolic acid-co-trimethylene carbonate), co-poly(ether-esters) (e.g. PEO/PLA), polyphosphazenes, biomolecules (such as fibrin, fibrinogen, cellulose, starch, collagen and hyaluronic acid), polyurethanes, silicones, polyesters, polyolefins, polyisobutylene and ethylene-alphaolefin copolymers, acrylic polymers and copolymers other than polyacrylates, vinyl halide polymers and copolymers (such as polyvinyl chloride), polyvinyl ethers (such as polyvinyl methyl ether), polyvinylidene halides (such as polyvinylidene chloride), polyacrylonitrile, polyvinyl ketones, polyvinyl aromatics (such as polystyrene), polyvinyl esters (such as polyvinyl acetate), acrylonitrile-styrene copolymers, ABS resins, polyamides (such as Nylon 66 and polycaprolactam), polycarbonates, polyoxymethylenes, polyimides, polyethers, polyurethanes, rayon, rayon-triacetate, cellulose, cellulose acetate, cellulose butyrate, cellulose acetate butyrate, cellophane, cellulose nitrate, cellulose propionate, cellulose ethers, and carboxymethyl cellulose. Additional representative examples of polymers that may be especially well suited for use in fabricating an implantable medical device according to the methods disclosed herein include ethylene vinyl alcohol copolymer (commonly known by the generic name EVOH or by the trade name EVAL), poly(butyl methacrylate), poly(vinylidene fluoride-co-hexafluororpropene) (e.g., SOLEF 21508, available from Solvay Solexis PVDF, Thorofare, N.J.), polyvinylidene fluoride (otherwise known as KYNAR, available from ATO-FINA Chemicals, Philadelphia, Pa.), ethylene-vinyl acetate copolymers, and polyethylene glycol.

In some embodiments, it may be desirable to manufacture an implantable stent that includes distinct regions that have different erosion profiles when exposed to bodily fluids. In this way the erosion profile of the stent may be customized to various treatments. Various embodiments of an implantable medical device with such erosion profiles may include a metallic region composed of a bioerodable metal, and a polymer region composed of a biodegradable polymer. The metallic region may be configured to erode at a different rate when exposed to bodily fluids than the polymer region when exposed to bodily fluids. In some embodiments, the polymer region may be configured to be an outer region or layer of the device and the metallic region may be an inner region or layer of the device. An outer region or layer may refer to a region or layer that is exposed first to a vascular environment. Direct contact or exposure of the inner region or layer to a vascular environment may be inhibited or prevented by an outer region or a region that is closer to the vascular environment. For example, a strut of a stent may include an inner region or core with an outer region or coating that inhibits or prevents direct contact or exposure of the inner region or core to a vascular environment. The metallic region may be configured to provide mechanical support for at least some of the time the device is implanted in a bodily lumen.

Fragmentation and Bioerosion

In some embodiments, the fragmentation process described above may be enabled in combination with the bioerosion process described above. In these embodiments a biostable coating, such as a teflon based compound, may be selectively applied to portions of a stent so as to leave other portions of the stent exposed to the moist environment of the peri-adventitial space. As a result of such selective coating, the exposed portions will be more prone to bioerosion than the coated portions. Thus, after a period of time, fragmentation of the stent at the uncoated portions will be accelerated in relation to the coated portions. This feature may be utilized to control the desired location of eventual fragmentation of the stent. Accordingly, by a strategic selection of portions to be coated or exposed, a stent such as that exemplified in FIGS. 7-9 may be constructed.

Figure 7:
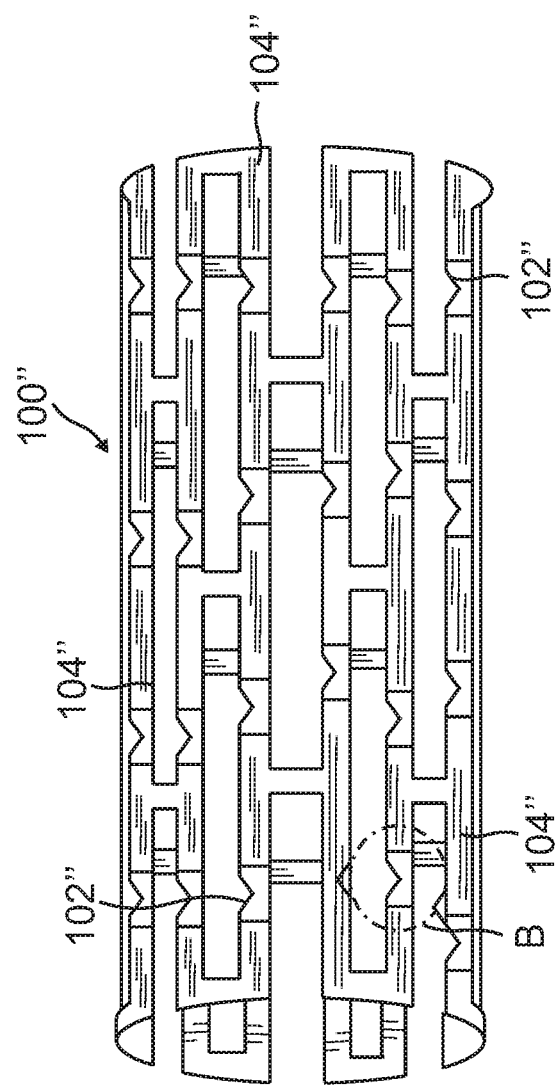
FIG. 7 is a perspective view of a stent having features according to another embodiment of the present invention.
Figure 8:
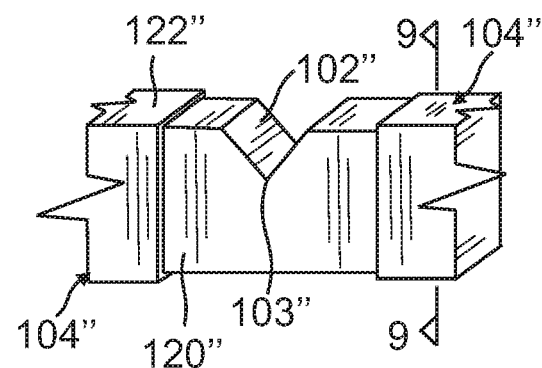
FIG. 8 is a detail view of a feature of the stent shown in FIG. 7, taken from the area marked as "B."
Figure 9:
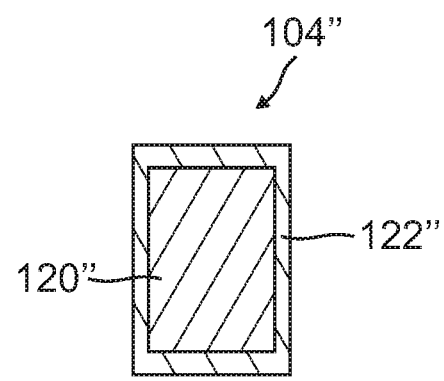
FIG. 9 is a sectional view taken substantially along the line marked 9-9 in FIG. 8.

FIG. 7 shows a schematic perspective view of a stent 100" having some of the features of the stent 100' seen in FIG. 4B. Similar to the stent 100' of FIG. 4B, the stent 100" of FIG. 7 has notches 102" cut into struts 104". These notches 102" are similarly designed to cause fragmentation of the stent 100" for the same reasons as set forth above. However, as best seen in FIGS. 8-9, in addition to the notches 102", stent 100" includes selectively located coating 122" which is configured to cover the metallic portion 120" of the struts 104" generally, but to be excluded from the area of the notches 102". The coating is designed to be biostable, and may include teflon compounds such as are known in the art when used to coat stents in their entirety.

In order to achieve selective coating of the stent with the coating 120", the stent may be manufactured as follows. After the stent has been cut from its initial tubular form, a small amount of an inert liquid wax like material such as paraffin wax may be applied to the region of the stent that includes the notch 120", or other area selected to eventually have no coating. After this process is complete, the entire stent may be coated with the selected biostable coating such as teflon based compound. Then, the coated stent may be placed in a heated fluid environment, preferably gaseous, until the stent is heated and the wax like material melts. At this point, a jet of fluid may be directed at the stent, to remove the coating which will be attached to the liquid wax. The net result is a stent which is coated over the majority of the strut area, but which is exposed in selected regions. It will be appreciated that in addition to selecting a notch region to receive no coating, other regions also may be selected to have no coating, according to specific design needs. The final result is a stent that is configured to fragment once it is implanted in the moist per-adventitial space, wherein the fragmentation commences in regions which are not coated with biostable coating, and which may, additionally be provided with notches to initiate crack propagation.

Heating

In other embodiments of the invention, once the aggressively oversized scaffold or stent has migrated to a desired extent through a vessel wall of a patient where it is positioned adjacent renal nerves, the scaffold may be heated by means known in the art such as induction heating by magnetic resonance, by ultrasound, or by RF signal induction. By heating the scaffold, additional denervation is applied to the nerves to provide the beneficial effects described herein.

The art of heating metal implants in a patient's body is a field that has been developed to some relatively high degree of sophistication, as disclosed for example in U.S. Pat. No. 6,786,904 (magnetic resonance), U.S. Pat. No. 6,451,044 (ultrasound), U.S. Pat. No. 6,238,421 (RF signal induction)—all of which are incorporated herein by reference. These, or similar, methods may be used in conjunction with the oversize scaffold of the present invention, and denervation that takes place due to mechanical interference with the nerves can, in addition, be enhanced by heating the nerves to further advance denervation.

Where magnetic resonance is to be used, the induction heating process may be carried out with a heating system as follows. The patient may be placed horizontally beneath a sending antenna configured to generate a magnetic field. Magnetic energy may be generated by a generator and amplifier unit, and electrical current is caused to flow to a resonant circuit which is preferably positioned close to the energy sending antenna. For the present purpose, the frequency range is preferably between 100 MHz and 900 MHz. During the inductive heating process, electric energy is transmitted to the metal stent by the magnetic field, which by the means of an induction coil flowing alternating current produces a magnetic alternating field, which consequently induces a certain current in the responsive metal stent. The electric energy supplied by the induction coil is first converted into magnetic energy, which is then converted into heat energy in the stent. The current density in the stent is determined through the so-called skin-effect. The highest current density is reached at the stent surface. The current density drops off inside the stent rapidly. This has the advantageous effect of localizing heat gain in the stent at the stent surface, where there is contact with the body tissue including renal nerves.

A suitable material for an oversized stent according to the principles of the present invention that can be effectively warmed by induction is, in some embodiments, an alloy of nickel and iron wherein the ratio of nickel to iron is selected to result in a magnetic permeability that generates the desired amount of heat in the spatial environment under which the system is configured to operate. In other embodiments, the stent may be formed from nickel-copper alloys, Nickel Palladium alloys, Palladium Cobalt alloys, and Nickel-Silicon alloys, where the ratio of metals in the alloys are selected according to the same principle.

Material Modification for Expansion Adjustment

In some embodiments of the invention, the described technique of heating metal implants in a patient's body may be applied for a further purpose. In some uses of embodiments of the invention as described herein, where an oversized stent is deployed in the renal artery of a patient with the purpose of modifying the function of the renal nerves, it is possible that the physician may determine that the stent has expanded to a degree at which adequate modification of the nerves has been achieved, or that additional expansion of the stent would be detrimental to the patient. In a case such as this, it is beneficial to provide a mechanism to enable the physician to terminate the continued expansion of the oversized stent.

Figure 10:
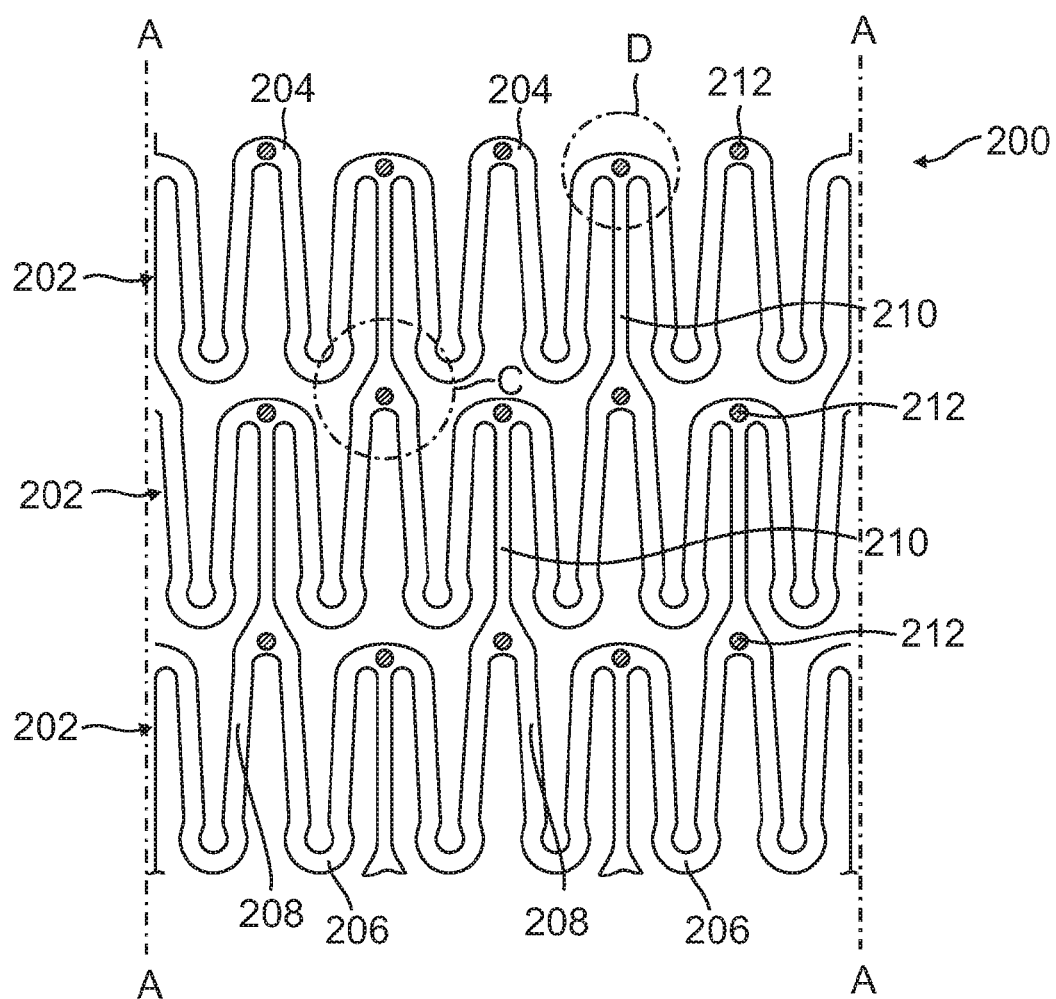
FIG. 10 is a "roll out" view of a stent of another embodiment having features of the invention.
Figure 11:
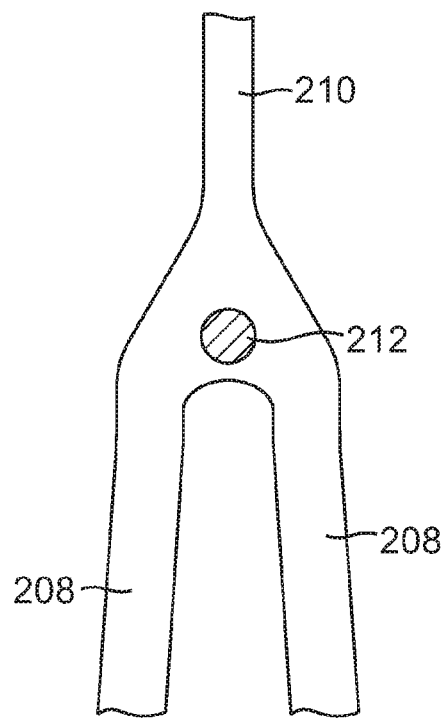
FIG. 11 is a detail view from FIG. 10, taken from the area marked as "C."
Figure 12:
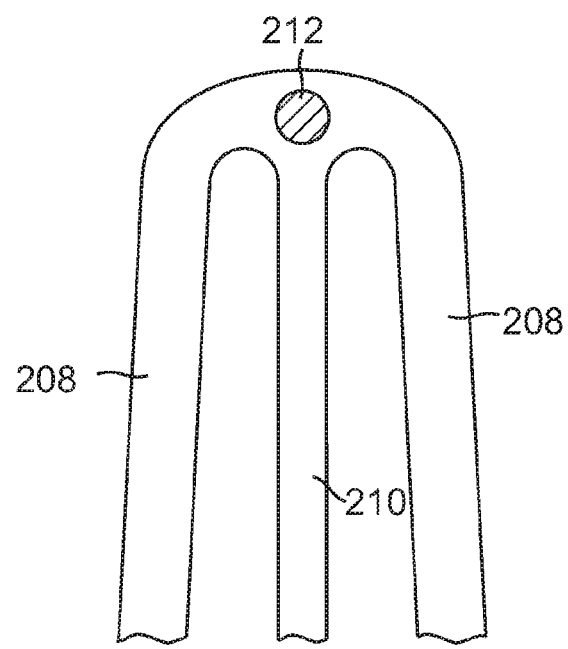
FIG. 12 is a detail view from FIG. 10, taken from the area marked as "D."
Figure 13:
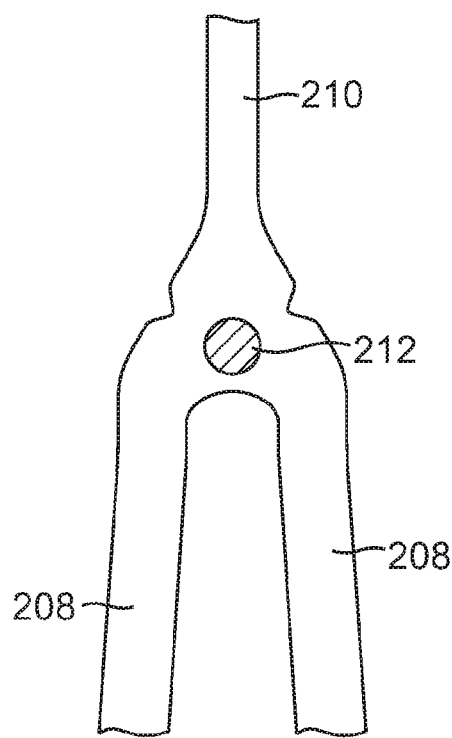
FIG. 13 is a detail view of another embodiment from FIG. 10, taken from the area marked as "C."
Figure 14:
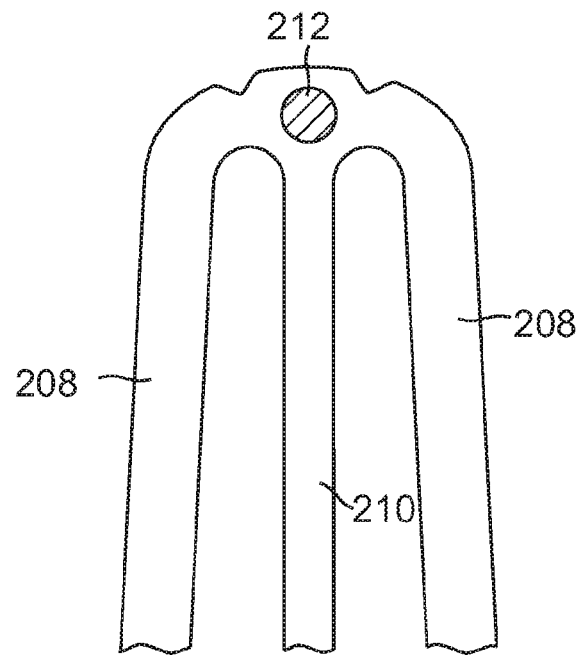
FIG. 14 is a detail view of another embodiment from FIG. 10, taken from the area marked as "D."

In order to accomplish this objective, a stent of a kind that is known in the art is modified in the following manner, as may be understood with reference to FIGS. 10-14. In FIG. 10, a stent 200 is depicted in "roll out" view, under which a cylindrical stent is envisaged as if it were rolled out onto a flat surface after being notionally split along an axially oriented line A-A on the surface of the stent. FIGS. 11-12 show details of FIG. 10. FIGS. 13-14 show another embodiment of the details in FIGS. 11-12. In some embodiments, the stent 200 comprises a plurality of annular rings 202 which extend around the circumference of the stent, and which are stacked one above the other and then connected to each other by links 210 to define a cylindrical profile. Each ring 202 comprises struts 208 that extend generally parallel with the axis of the stent. Each strut 208 is connected to an adjacent strut at their upper ends by a curved peak 204, and at their lower ends by a curved valley 206. The result is a ring 202 that comprises a strip of material that follows a serpentine path around the circumference of the stent. As in the case of the stents exemplified above, the stent is in some embodiments a self-expanding stent that is compressed into a smaller delivery diameter for insertion into a delivery catheter, and which will self-expand to a larger deployed diameter in the renal artery when the stent is released from the catheter at a desired location within the renal artery.

Just as with previous embodiments, the stent 200 is selected to self-expand to a size that will exceed the size of the renal artery into which it will be delivered, in order to affect a modification to the function of the renal nerves by applying mechanical pressure to the nerves.

However, in one embodiment, a polymer is used to form the self-expanding stent. With respect to polymeric stents, a number of manufacturing methods have been employed. In one method, the polymeric stent may be formed by laser cutting a flat polymeric sheet in the form of rings and links, subsequently rolling the pattern into the shape of the cylindrical stent and then providing a longitudinal weld to form the stent. In another method, a flat polymeric sheet may be chemically etched and then subsequently rolled and welded to form the polymeric stent. Alternatively, a polymeric wire may be coiled to form a polymeric stent. In yet another method, a polymeric stent may be formed from a tube by laser cutting a pattern of cylindrical rings and connecting links in the tube itself. See, e.g., U.S. Pat. No. 6,585,755 to Jackson et al. the contents are which are incorporated herein by reference.

During fabrication of the polymeric stent, a plug 212 of a metal that is susceptible to inductive heating via magnetic resonance from a remote energy source is inserted through the wall of the stent. The plug may be inserted into a pre-drilled hole in the wall of the stent, and then pressure may be applied from either end to squeeze and expand the plug, much like a rivet is installed in a sheet of metal. Notably, in some embodiments, the plug 212 is inserted into the stent at a location where the maximum bending moment in the expanded stent will be anticipated. In the example shown in FIGS. 10-14, that location will be in the peaks and the valleys of the rings where the maximum deformation in the stent can be expected to take place upon expansion. It will be appreciated that, when the stent is fully expanded into a body lumen, the walls of the body lumen will tend to apply a resistant force on the stent that tends to reduce the size of the stent. As will be appreciated, this will cause bending moments to be maximized at the turning points of the serpentine structure (i.e. the peaks and valleys) that makes up the rings of the stent.

During the process of treatment of a patient under which the present method of treatment by oversized stent is applied, the treating physician will observe the expansion of the stent using known visualization techniques such as fluoroscopy. Simultaneously, the treating physician will monitor the treatment regime and the degree of response of the patient. Should the physician decide that expansion of the stent has reached a degree beyond which further expansion would be unnecessary or undesirable, she may decide to apply an external energy source which is designed to induce a sympathetic response in the plugs 212, and cause them to gradually become heated. In this regard, the same technology may be used for heating the plugs 212 as is described above for heating an entire stent, with reference to U.S. Pat. No. 6,786,904 (magnetic resonance), U.S. Pat. No. 6,451,044 (ultrasound), U.S. Pat. No. 6,238,421 (RF signal induction).

The effect of heating the plugs 212 is to cause the surrounding material of the polymer stent to locally exceed its glass-transition temperature at locations near the heated elements. For Poly-L-lactide polymers, the glass-transition temperature may be approximately 40-50 degrees C. This effect weakens or "ages" the structure and locally reduces the polymer chain molecular weight in critical locations of the structure because when the stent 200 is expanded and positioned within the peri-advential space, the location of the plugs 212 in the peaks 204 and the valleys 206 of the rings 202 are located in the material of the stent where the bending moments and the stresses are typically the highest in the stent. Thus, weakening the material of the stent in these critical locations causes the stent 200 to relax its radially outward expansion force by reducing the elastic modulus locally, with the result that the diameter of the stent ceases to expand, or may even contract slightly to reduce the radially outward force exerted by the stent on the renal nerves.

Thus the physician, by applying heat energy to the plugs, has the ability to cause the outward expansion force of the stent to cease or to be reduced.

In another embodiment, a Nitinol (or other metallic) scaffold may be similarly configured to contain heating elements or plugs 212 at the crest features (peaks and valleys) of the design. In this case, when the scaffold reaches a target diameter coincident with the location of nerves in the peri-adventitial space, the application of external inductive heating accomplishes the result that the scaffold locally exceeds its heat-set/transformation temperature at locations near the plugs 212, thereby reducing the structural properties of the stent in the form of the modulus of elasticity. This second function weakens the structure and limits its tendency to expand further than is desired and may employ a preferred specific heat-set geometry. In this aspect, it should be noted that materials with a higher magnetic resonance susceptibility than that of the stent itself should be incorporated in the plug features. Furthermore, sharper geometric features should be incorporated in the plugs to further exacerbate local heat-up. For Nitinol features, applying heat treatment history to setting an austenite finish temperature which is higher than the expected range of body temperature (approximately 50 deg. C. or higher) will allow for selective weakening of the structure to prevent further outward expansion.

In yet another embodiment, applicable to a stent that is formed either from a polymer or from Nitinol or other metallic scaffold is similarly configured to contain heating elements or plugs. However, in this embodiment, the material surrounding the plugs is locally narrowed by the inclusion of localized notches 216 so that only a thin segment of material surrounds the plug, as exemplified in FIGS. 13-14. Thus, when the scaffold reaches a target diameter coincident with the location of nerves in the peri-adventitial space, the application of external inductive heating, as previously described, induces thermal weakening in the structure at the locally narrowed locations near the heated elements, thereby inducing localized fractures in the key scaffold features that are employed to provide radial strength.

The purpose of fragmenting the stent by the means and method described is the same as that purpose set forth above in relation to the embodiments exemplified in FIGS. 4B, 5, 7, and 8, under which the presence of fractured stent struts in the peri-adventitial space is configured to disrupt or modulate neural function by inducing sharpened pressure on the nerves and surrounding tissues, such sharpened pressure being applied by independently movable strut portions that have fractured and broken away from the original stent.

Thus there is provided a convenient and advantageous system and method for modifying the outward force applied by a stent that is being used to modify the function of the renal nerves of a patient by applying physical pressure on the nerves.

Drug Elution

In yet a further embodiment of the invention, the oversize scaffold may be configured so that, once it has migrated to a desired extent through a vessel wall of a patient where it is positioned adjacent renal nerves, the scaffold elutes known neurotoxic drugs which are taken up by the renal nerves to cause denervation. The art of injecting neurotoxic drugs into a patient's body for purposes of neuromudulation is a field that has been developed to a relatively high degree of sophistication, as disclosed for example in U.S. Pat. No. 7,162,303. Furthermore, the art of fabricating stents that will elute therapeutic drugs into a patient's vascular system and related tissue has also been developed, as disclosed for example in U.S. Pat. Nos. 7,807,722 and 8,187,322 which are incorporated herein by reference. These, or similar methods may be used in conjunction with the oversize scaffold of the present invention, and denervation that takes place due to mechanical interference within the nerves can be enhanced by, in addition, application of neurotoxic agents by elution from the implanted stent.

Thus, the embodiments described provide an advantageous system and method for stimulating and blocking renal nerves, and thereby providing a therapeutic result for patients suffering from ailments including acute myocardial infarction, heart failure, chronic renal failure and hypertension. The present invention may, of course, be carried out in other specific ways than those herein set forth without departing from the essential characteristics of the invention. The present embodiments are, therefore, to be considered in all respects as illustrative and not restrictive, while the scope of the invention is set forth in the claims that follow.

We claim:

1. A method for treating a patient diagnosed with a cardio-renal disease or disorder, the method comprising:
   a. selecting a span of a renal artery in the patient for implantation of a self-expanding stent, the renal artery having a first internal diameter, an artery wall, and being surrounded by a peri-adventitial space through which at least one renal nerve extends;
   b. measuring the first internal diameter;
   c. selecting a self-expanding stent having a cylindrical outer surface, the stent being configured to have a first external diameter in an unexpanded condition and being capable of expanding to have a second external diameter, wherein the second external diameter once the stent is implanted within the artery, is larger than the first internal diameter;
   d. implanting the stent in the span of the renal artery, whereby the stent eventually expands towards the second external diameter and thereby passes through the artery wall to become embedded in the peri-advential space surrounding the artery; and
   e. applying pressure to the at least one renal nerve with the stent, thereby at least partially modulating a function of the at least one renal nerve;
   f. reducing an elastic modulus of the stent when the stent has the second external diameter.

2. The method of claim 1, wherein reducing an elastic modulus of the stent includes heating a portion of the stent.

3. The method of claim 2, wherein heating a portion of the stent includes applying an electromagnetic field to the stent.

4. The method of claim 2, wherein heating a portion of the stent includes applying ultrasonic energy to the stent.

5. The method of claim 2, wherein heating a portion of the stent includes applying a radio frequency signal to the stent.

6. The method of claim 2, wherein heating a portion of the stent includes positioning a metal element in a structural component of the stent.

7. The method of claim 2, wherein reducing an elastic modulus of the stent includes reducing an elastic modulus of the stent to a level at which the stent fractures.

* * * * *